(12) United States Patent
Suzuma et al.

(10) Patent No.: US 8,466,674 B2
(45) Date of Patent: Jun. 18, 2013

(54) MAGNETIC TESTING METHOD AND MAGNETIC TESTING APPARATUS

(75) Inventors: Toshiyuki Suzuma, Osaka (JP); Kenji Imanishi, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 299 days.

(21) Appl. No.: 12/992,618

(22) PCT Filed: May 14, 2009

(86) PCT No.: PCT/JP2009/058969
§ 371 (c)(1),
(2), (4) Date: Feb. 28, 2011

(87) PCT Pub. No.: WO2009/139432
PCT Pub. Date: Nov. 19, 2009

(65) Prior Publication Data
US 2011/0163741 A1 Jul. 7, 2011

(30) Foreign Application Priority Data
May 15, 2008 (JP) ................................ 2008-128523

(51) Int. Cl.
*G01N 27/82* (2006.01)
(52) U.S. Cl.
USPC ......................................... 324/240; 324/238

(58) Field of Classification Search
USPC .................................................. 324/238, 240
See application file for complete search history.

(56) References Cited

U.S. PATENT DOCUMENTS

| | | | | |
|---|---|---|---|---|
| 4,818,935 A | * | 4/1989 | Takahashi et al. | 324/232 |
| 2006/0152216 A1 | * | 7/2006 | Higuchi | 324/237 |

FOREIGN PATENT DOCUMENTS

| | | |
|---|---|---|
| JP | 62-145162 | 6/1987 |
| JP | 2-66446 | 3/1990 |
| JP | 2002-131285 | 5/2002 |
| JP | 2005-164516 | 6/2005 |

\* cited by examiner

*Primary Examiner* — Bot Ledynh
(74) *Attorney, Agent, or Firm* — Clark & Brody

(57) ABSTRACT

A magnetic testing apparatus has a magnetizing device applying a rotating magnetic field to a material to be tested, a testing signal detecting device, and a signal processing device applying signal processing to the testing signal. The signal processing device has a first synchronous detecting device detecting a testing signal by using the first current as a reference signal, a second synchronous detecting device detecting an output signal of the first synchronous detecting device by using the second current as a reference signal to extract a candidate flaw signal, and a testing image display device displaying a testing image in which each of pixels has a gray level corresponding to an intensity of the candidate flaw signal at each of positions of the material to be tested, and a phase of the candidate flaw signal at each of the positions is capable of being identified.

8 Claims, 13 Drawing Sheets

MAGNETIC TESTING METHOD AND MAGNETIC TESTING APPARATUS

BACKGROUND OF THE INVENTION

1. Field of the Invention

The present invention relates to a magnetic testing method and a magnetic testing apparatus which can detect flaws existing in a material to be tested and extending in various directions with high precision by using a rotating magnetic field.

2. Description of the Related Art

Conventionally, as a method of detecting a flaw existing in a material to be tested such as a steel plate, a steel pipe or tube or the like in a nondestructive manner, there have been known magnetic testing methods such as an eddy current testing method, a magnetic flux leakage testing method and the like. The eddy current testing method is a testing method utilizing a fact that an eddy current induced by applying an alternating magnetic field to a material to be tested is disturbed by the flaw. Further, the magnetic flux leakage testing method is a testing method utilizing a fact that in the case that a magnetic field is applied to a material to be tested made of a magnetic body so as to magnetize, if a flaw blocking the magnetic flux generated in the material to be tested exists, the magnetic flux leaks to a surface space at a position where the flaw exists.

In the magnetic testing method, in general, an amplitude of a flaw signal to be detected (a signal obtained from the position where the flaw exists, in testing signals detected by a predetermined detection sensor) becomes maximum, in the case that a direction of the applied magnetic field forms a particular angle with respect to a direction in which the flaw extends. For example, the amplitude of the flaw signal in the magnetic flux leakage testing method becomes maximum in the case that the direction of the applied magnetic field (the direction of the magnetic flux in the material to be tested) is orthogonal to the flaw extending direction, and is lowered in accordance with that the direction of the magnetic field deflects from the direction which is orthogonal to the flaw extending direction.

Accordingly, in order to detect (in order to obtain a detectable amplitude of a flaw signal) whatever direction the flaw extends, there has been proposed a magnetic testing method of applying a rotating magnetic field in which a direction of the magnetic field changes hour by hour to the material to be tested, and detecting the flaws extending in the various directions, based on a testing signal generated by the rotating magnetic field (for example, refer to Japanese Unexamined Patent Publication No. 2002-131285).

In order to generate the rotating magnetic field mentioned above, for example, an exciting coil as shown in FIG. 1 is used. In other words, an exciting coil 10 shown in FIG. 1 is provided with two exciting coils (an X direction exciting coil 1 and a Y direction exciting coil 2) arranged in such a manner that winding directions of lead wires are orthogonal to each other (accordingly, generated magnetic fields are orthogonal to each other), and center positions coincide with each other. Further, a resultant magnetic field of the magnetic fields generated in the exciting coils 1 and 2 rotates 360 degrees around the center positions of the exciting coils 1 and 2 (an angle φ shown in FIG. 1 changes between 0 and 360 degrees), by shifting a phase of an alternating exciting current applied to the exciting coils 1 and 2 by 90 degrees (for example, applying a cosine wave exciting current to the X direction exciting coil 1, and applying a sine wave exciting current to the Y direction exciting coil 2). Accordingly, it is possible to detect the flaws extending in various directions (an angle θ shown in FIG. 1 is between 0 and 360 degrees).

In the meantime, in general, in the case that a signal to be detected (a flaw signal in the case of the magnetic testing method) has a specific frequency component with respect to a signal constituted by various frequency components including a noise, it is often the case that a synchronous detection is used for extracting a signal having the specific frequency component.

In the conventional magnetic testing method which does not utilize the rotating magnetic field, the flaw signal is synchronized with the alternating exciting current. Accordingly, it is possible to extract a flaw signal from a testing signal at a high S/N ratio by synchronously detecting the testing signal by using the exciting current as a reference signal, and extracting a signal which is synchronized with the exciting current. Further, the alternating current signal extracted by the synchronous detection is generally smoothened by a low-pass filter, in order to make a ratio (S/N ratio) between the flaw signal and the noise generated in a random order without being synchronized with the exciting current higher. Preferably, the alternating signal extracted by the synchronous detection is smoothened per unit region corresponding to about two or three cycles of the reference signal (the exciting current), by regulating a time constant of the low-pass filter.

Further, in the eddy current testing method, a phase analysis method is generally used as a method for improving a flaw detection performance by using the signal obtained by synchronously detecting the testing signal. In this phase analysis method, an X signal is set to a signal obtained by synchronously detecting the testing signal using the reference signal, and a Y signal is set to a signal obtained by delaying the phase of the reference signal by 90 degrees so as to synchronously detect the testing signal. Further, the method measures how long the phase of the testing signal is delayed with respect to the reference signal, by setting the X signal to an X-axis component, setting the Y signal to a Y-axis component, and displaying the signal by vector on a two-dimensional plane of an X-Y coordinate system (a locus of a vector leading end is referred to as a Lissajous waveform). For example, in the case of synchronously detecting the testing signal having the same phase as the reference signal, it is possible to obtain the Lissajous waveform extending along the X axis as shown in FIG. 2A because of no phase delay. More specifically, in the case of the flaw signal, since the phase is inverted by 180 degrees when the detection sensor passes just above the flaw, it is possible to obtain the Lissajous waveform extending along a direction 0 degrees (a positive direction of the X axis) and a direction 180 degrees (a negative direction of the X axis). In the same manner, with regard to the testing signal in which the phase is delayed by 45 degrees with respect to the reference signal, it is possible to obtain the Lissajous waveform extending along a direction 45 degrees and a direction 225 degrees as shown in FIG. 2B. Further, with regard to the testing signal in which the phase is delayed by 90 degrees, it is possible to obtain the Lissajous waveform extending along a direction 90 degrees and a direction 270 degrees as shown in FIG. 2C.

At this point, it is a rare case that a phase of the flaw signal detected by the magnetic testing method (that is, a signal caused by a turbulence of the eddy current by the flaw, and a signal corresponding to the leakage magnetic flux by the flaw) becomes absolutely identical to a phase of a liftoff varying noise (a fluctuation of the testing signal generated in the case of varying a clearance between the detection sensor and the material to be tested) corresponding to one kind of main noises at a time of testing, and they generally have a phase difference. FIGS. 3A and 3B are schematic views of the Lissajous waveform indicating the fact that the flaw signal and the liftoff varying noise have the phase difference. As shown in FIG. 3A, it is general that a phase φd of the flaw signal is different from a phase φl of the liftoff varying noise. Further, as shown in FIG. 3A, if the amplitude of the flaw signal is set to Ad, and the amplitude of the liftoff varying noise is set to Al, the S/N ratio (=Ad/Al) becomes about 1.5 in this example. However, as shown in FIG. 3B, since the S/N ratio (=Sd/Sl) becomes larger than 10 in this example, by rotating the X-Y coordinate system in such a manner that the liftoff varying noise extends along the X axis, and setting a signal component in a direction Y'-axis in the X'-Y' coordinate system after the rotation to the testing signal, the S/N ratio is widely improved in comparison with the case that the S/N ratio is evaluated by the amplitude (FIG. 3A). As mentioned above, there can be expected that it is possible to suppress an influence of the liftoff varying noise with respect to the flaw detection performance, by applying the phase analysis method.

Further, the phase analysis method includes a method of evaluating only an amplitude of a signal component having a specific phase in the Lissajous waveform, and excluding the amplitude of the signal component having the other phase from the subject to be evaluated, in addition to the method of rotating the X-Y coordinate system of the Lissajous waveform as mentioned above.

However, the conventional magnetic testing method utilizing the rotating magnetic field has the following problems due to using the exciting current having the single frequency.

(1) Since it is not possible to sufficiently obtain the effect of the synchronous detection, there is a risk that the flaw detection performance (S/N ratio) is lowered.

(2) It is not possible to estimate an angle information of the flaw (what direction the flaw extends in).

(3) It is not possible to use the phase analysis method which is general as a method of improving the flaw detection performance (S/N ratio) in the eddy current testing method.

(4) It is not possible to accurately evaluate a continuity of the flaw.

Therefore, in accordance with the conventional magnetic testing method utilizing the rotating magnetic field, it is possible to conceptually detect the flaws extending in the various directions, however, it cannot be said that the flaw detection performance is practically sufficient. Further, since it is not possible to estimate the angle information of the flaw, it is hard to determine a cause by which the flaw is generated. A description will be specifically given below of the problems (1) to (4).

As mentioned above, in the magnetic testing method, in general, the amplitude of the detected flaw signal becomes maximum in the case that the direction of the applied magnetic field forms a specific angle with respect to the direction in which the flaw extends. In this case, it is assumed that the amplitude of the flaw signal comes to 0 if an angle of shift of the direction of the magnetic field from the direction in which the amplitude of the flaw signal becomes maximum cuts across ±α degree. In the conventional magnetic testing method utilizing the rotating magnetic field generated by the exciting current having the single frequency using the exciting coil 10 as shown in FIG. 1, since the direction of the magnetic field is rotated by 360 degrees during one cycle of the exciting current, the flaw signal appears (the amplitude of the flaw signal becomes larger than 0) under the assumption mentioned above only in a specific range in one cycle of the exciting current (a range in which the direction of the magnetic field between −α degree and +α degree can be obtained based on the direction in which the amplitude of the flaw signal becomes maximum).

In this case, it is assumed that two kinds of flaws A and B (an angle θ (see FIG. 1) of a flaw A equals to 20 degrees, and an angle θ of a flaw B equals to 70 degrees) having different extending directions exist in the material to be tested, and the angle α equals to 20 degrees. As mentioned above, since the amplitude of the flaw signal in the magnetic flux leakage testing method becomes maximum in the case that the direction of the applied magnetic field is orthogonal to the flaw extending direction, the flaw signal of the flaw A becomes maximum in the case that the direction φ (see FIG. 1) of the magnetic field satisfies a relation φ=20 degrees+90 degrees+180 degrees×n (n is an integral number) under the assumption mentioned above, and the amplitude comes to 0 if it goes beyond the range φ±20 degrees. In the same manner, the flaw signal of the flaw B becomes maximum in the case that the direction φ of the magnetic field satisfies a relation φ=70 degrees+90 degrees+180 degrees×n (n is an integral number), and the amplitude comes to 0 if it goes beyond the range φ±20 degrees.

FIG. 4 is a graph showing a time sequence relation between the exciting current waveform and the flaw signal waveform, under the assumption mentioned above. Further, FIGS. 5A and 5B are graphs each showing a flaw signal waveform after synchronously detecting the testing signal including the flaw signal by using the exciting current as the reference signal, and smoothening the flaw signal extracted by the synchronous detection per unit region corresponding to two cycles of the reference signal. FIG. 5A shows the flaw signal waveform of the flaw A, and FIG. 5B shows the flaw signal waveform of the flaw B. In this case, in FIGS. 4, 5A and 5B, an illustration of the noise waveform included in the testing signal is omitted.

In the case of synchronously detecting the testing signal, the synchronous detection uses the exciting current applied to the X direction exciting coil 1 shown in FIG. 1, or the exciting current applied to the Y direction exciting coil 2 as the reference signal, however, as can be seen from FIG. 4, the flaw signals obtained from the flaws A and B are shorter in the cycle than any exciting current. In other words, since the cycle of the flaw signal does not coincide with the cycle of the reference signal, it is not possible to sufficiently obtain the effect of the synchronous detection (the effect of extracting the flaw signal from the testing signal at the high S/N ratio), and there is a risk that the flaw detection performance is lowered (the problem (1) mentioned above).

Further, in the case of smoothening the flaw signal extracted by the synchronous detection per unit region corresponding to two cycles of the reference signal, as shown in FIGS. 5A and 5B, the phase information of the flaw signal (the angle information of the flaw) after smoothening is lost, and the flaw signals after smoothening come to a similar direct current signal waveform in both of flaws A and B. In other words, the angle information of the flaw cannot be estimated (the problem (2) mentioned above).

Further, since the phase information of the flaw signal after smoothening is lost as mentioned above, and it is not possible to specify what position the flaw signal exists in one cycle of the exciting current, it is necessary to always evaluate based on the ratio between the amplitude of the flaw signal and the amplitude of the noise as mentioned above with reference to FIG. 3A, at a time of evaluating the flaw detection performance (S/N ratio). In other words, the general phase analysis method cannot be used as the method of improving the flaw detection performance (the problem (3) mentioned above).

Further, there has been conventionally proposed a method of comprehending a two-dimensional distribution state of the flaw based on a testing image, and evaluating a continuity of the flaw, for the purpose of accurately evaluating the continuity of the flaw so as to improve a flaw detection precision. Specifically, this method forms a testing image (a gray image or a color image) by imaging the testing signal including the flaw signal or by imaging a signal obtained by binarizing the testing signal by a predetermined threshold value. And this method comprehends the two-dimensional distribution state of the flaw and evaluates the continuity of the flaw, by visually observing the testing image, or applying an image process using an appropriate image processing filter or the like to the testing image. This is because there is a case that a plurality of flaws (group defects) extending in the same direction are recognized as one flaw, and a length of a whole of the group defects is recognized as an evaluation index of a harmfulness, in addition to the evaluation of a depth and a length of the individual flaw segmented and detected at a time of evaluating the harmfulness of the flaw. This index is provided for evaluating the harmfulness higher in comparison with the flaw which is actually segmented, in the case where the flaws are actually constructed by one continuous flaw, even if the flaws are segmented into a plurality of pieces and detected. Accordingly, it is important to accurately evaluate the length of the whole of the group defects, that is, the continuity of the flaw.

However, in the conventional magnetic testing method utilizing the rotating magnetic field, since it is not possible to estimate the angle information of the flaw as mentioned above, it is necessary to form the testing image based on only the amplitude information of the testing signal. Accordingly, with regard to the flaw which is detected in the segmented manner, for example, due to a partial small depth of the flaw in spite that the flaw is actually constituted by a single continuous flaw, and is displayed in the segmented manner in the testing image, it is hard to accurately evaluate the continuity of the flaw (the problem (4) mentioned above). Particularly, in the case that position resolution of the testing image cannot help lowering (common case from a restriction of a detection efficiency in the line feeding the material to be tested at a high speed), since it is not possible to set a scanning interval of a detection sensor which is sufficiently small in comparison with a dimension of the flaw, it is not possible to obtain an accurate information what direction the flaw extends, based on the testing image itself. Accordingly, it is hard to accurately evaluate the continuity of the flaw. A description will be more specifically given below with reference to FIGS. 6 to 8.

As shown in FIG. 6, there is assumed a case that two flaws A and B and a noise source N exist in a material to be tested S. Further, there is assumed that pixel groups exist within a testing image obtained by scanning the detection sensor on the material S (a testing image imaging the signal obtained by binarizing the testing signal by a predetermined threshold value), as shown in FIG. 7. The pixel groups are discretized in correspondence to an A/D conversion speed, a scanning speed or the like of the detection sensor, and correspond to a candidate flaw position in the material S. In other words, the pixel groups are constituted by four pixel groups a1 to a4 corresponding to the flaw A, two pixel groups b1 and b2 corresponding to the flaw B, and a pixel n corresponding to the noise source N.

In the case of evaluating the continuity of the flaw with respect to the testing image shown in FIG. 7, since the testing image is formed only based on the amplitude information of the testing signal, the continuity cannot help being evaluated only based on the distribution state of the pixel groups corresponding to the candidate flaw position. Accordingly, there is a risk that the pixel groups a1 to a4 and b1 are erroneously evaluated as one flaw A, and the pixel groups b2 and n are erroneously evaluated as one flaw B, as shown in FIG. 8, in correspondence to the structure of the image processing filter or the like for evaluating the continuity of the flaw. In other words, there is a risk that the pixel n corresponding to the noise source N is erroneously recognized as the flaw, as well as the length of the flaw A is evaluated to be larger than the actual length and the length of the flaw B is evaluated to be smaller than the actual length. Accordingly, there is a risk that the harmfulness of the flaw cannot be accurately evaluated.

SUMMARY OF THE INVENTION

The present invention has been devised to solve the problems of the related art, and an object of the present invention is to provide a magnetic testing method and a magnetic testing apparatus which can precisely detect flaws existing in a material to be tested and extending in various directions by using a rotating magnetic field.

In order to achieve the object, the present invention provides a magnetic testing method applying a rotating magnetic field to a material to be tested and detecting a flaw based on a testing signal generated by the rotating magnetic field, the method comprising the steps of extracting a candidate flaw signal by using an alternating current obtained by superimposing a first current and a second current having a lower frequency than the first current, as an exciting current for exciting the rotating magnetic field, synchronously detecting the testing signal by using the first current as a reference signal, and thereafter synchronously detecting by using the second current as a reference signal; displaying a testing image constructed by a plurality of pixels corresponding to respective positions of the material to be tested, each of the pixels having a gray level corresponding to an intensity of the candidate flaw signal at each of the positions, and a phase of the candidate flaw signal at each of the positions in the testing image being capable of being identified; and detecting the flaw based on the displayed testing image.

In accordance with the invention mentioned above, since the alternating current obtained by superimposing the first current and the second current which has the lower frequency than the first current is used as the exciting current for exciting the rotating magnetic field, the magnetic field generated by the first current having the high frequency (and the eddy current induced by the magnetic field) predominantly acts on the material to be tested, and the second current having the low frequency functions for mainly rotating the direction of the generated magnetic field (and the eddy current) in the material to be tested. This is because the induced electromotive force generated in the material to be tested is in proportion to the frequency of the exciting current.

Further, in accordance with the present invention, the candidate flaw signal is extracted by synchronously detecting the testing signal by using the first current as the reference signal and thereafter synchronously detecting by using the second current as the reference signal. In other words, since the testing signal is synchronously detected at the first setout by using the first current having the higher frequency than the rotating frequency (corresponding to the frequency of the second current) of the magnetic field as the reference signal, it is easy to bring the cycle component included in the flaw signal obtained from the position at which the flaw actually exists into line with the cycle of the reference signal, in comparison with the conventional case of synchronously detecting based on the reference signal having the same frequency as the rotating frequency of the magnetic field, and there can be expected that it is possible to sufficiently obtain the effect (extracting the flaw signal from the testing signal at the high S/N ratio) of the synchronous detection. Further, since the phase information of the flaw signal included in the smoothened testing signal tends to be held even by smoothening the testing signal extracted by synchronously detecting by using the first current as the reference signal per unit region corresponding to about two or three cycles of the reference signal, it is possible to estimate the angle information of the flaw (what direction the flaw extends in). Further, since the phase information of the flaw signal tends to be held even by smoothening as mentioned above, it is possible to apply the phase analysis method at a time of synchronously detecting successively by using the second current as the reference signal, and it is possible to suppress the influence of the liftoff varying noise or the like applied to the flaw detection performance.

Further, in accordance with the present invention, there is displayed the testing image constructed by a plurality of pixels corresponding to the respective positions of the material to be tested. Each of the pixels has the gray level corresponding to the intensity of the candidate flaw signal (the testing signal after synchronously detecting by using the second current as the reference signal) at each of the positions (including the case that the intensity of the candidate flaw signal is binarized by the predetermined threshold value). The phase of the candidate flaw signal at each of the positions can be identified in the teting image. Specifically, for example, one color image is displayed as the testing image, the color image being structured such that the pixels are colored into the different colors in correspondence to the phase of the candidate flaw signal obtained by applying the phase analysis method (the gray level of each of the pixels is different in correspondence to the intensity of the candidate flaw signal). Alternatively, a plurality of gray images in which the phase (the range of phase) of the candidate flaw signal included in each of the images is different (the gray level of each of the pixels is different in correspondence to the intensity of the candidate flaw signal) are displayed as the testing image. Accordingly, since it is possible to visual observe the phase (the angle information) in addition to the intensity of the candidate flaw signal in the testing image, it is possible to accurately evaluate the continuity of the flaw.

Further, in order to achieve the object, the present invention also provides a magnetic testing method applying a rotating magnetic field to a material to be tested and detecting a flaw based on a testing signal generated by the rotating magnetic field, the method comprising the steps of: extracting a candidate flaw signal by using an alternating current obtained by superimposing a first current and a second current having a lower frequency than the first current, as an exciting current for exciting the rotating magnetic field, synchronously detecting the testing signal by using the first current as a reference signal, and thereafter synchronously detecting by using the second current as a reference signal; detecting a candidate flaw position in the material to be tested by binarizing the candidate flaw signal by a predetermined threshold value; forming a plurality of testing images which are constructed by a plurality of pixels corresponding to respective positions of the material to be tested, the corresponding pixel to the detected candidate flaw position having a gray level capable of being identified from the other pixels, in correspondence to a phase of the candidate flaw signal at the candidate flaw position; evaluating a continuity of the candidate flaw position with regard to a direction corresponding to the phase of the candidate flaw signal at the candidate flaw position existing in each of the testing images, by individually applying an image processing to each of the testing images; and detecting the flaw based on the continuity of the candidate flaw position.

In accordance with the invention as mentioned above, it is possible to expect that the effect of the synchronous detection can be sufficiently obtained, in the same manner as mentioned above, to estimate the angle information of the flaw, and to suppress the influence of the liftoff varying noise or the like with respect to the flaw detection performance. Further, it is possible to automatically and accurately evaluate the continuity of the flaw in accordance with the image processing.

In this case, the ratio between the frequency of the first current and the frequency of the second current may be appropriately decided based on what resolution the angle information of the flaw is estimated (the greater the ratio between the both is, the larger the resolution is). For example, in order to estimate the resolution of at least 45 degrees pitch, it is necessary to set the ratio between the both equal to or more than 8 (360 degrees/45 degrees=8).

Therefore, preferably, in the magnetic testing method, frequencies of the first current and the second current satisfy the following equation (1).

$$\text{frequency of first current/frequency of second current} \geq 8 \quad (1)$$

Further, in order to achieve the object, the present invention also provides a magnetic testing apparatus comprising: a magnetizing device applying a rotating magnetic field to a material to be tested; a detecting device detecting a testing signal generated by the rotating magnetic field; and a signal processing device applying a signal processing to the testing signal, wherein the magnetizing device is provided with an exciting coil applying an alternating current obtained by superimposing a first current and a second current having a lower frequency than the first current as an exciting current, and wherein the signal processing device includes: a first synchronous detecting device synchronously detecting the testing signal detected by the detecting device by using the first current as a reference signal; a second synchronous detecting device synchronously detecting an output signal of the first synchronous detecting device by using the second current as a reference signal so as to extract a candidate flaw signal; and a testing image display device displaying a testing image constructed by a plurality of pixels corresponding to respective positions of the material to be tested, each of the pixels having a gray level corresponding to an intensity of the candidate flaw signal at each of the positions, and a phase of the candidate flaw signal at each of the positions in the testing image being capable of being identified.

Further, in order to achieve the object, the present invention also provides a magnetic testing apparatus comprising: a magnetizing device applying a rotating magnetic field to a material to be tested; a detecting device detecting a testing signal generated by the rotating magnetic field; and a signal processing device applying a signal processing to the testing signal, wherein the magnetizing device is provided with an exciting coil applying an alternating current obtained by superimposing a first current and a second current having a lower frequency than the first current as an exciting current, and wherein the signal processing device includes: a first synchronous detecting device synchronously detecting the testing signal detected by the detecting device by using the first current as a reference signal; a second synchronous detecting device synchronously detecting an output signal of the first synchronous detecting device by using the second current as a reference signal so as to extract a candidate flaw signal; a candidate flaw position detecting device detecting a candidate flaw position in the material to be tested by binarizing the candidate flaw signal by a predetermined threshold value; a testing image forming device forming a plurality of testing images which are constructed by a plurality of pixels corresponding to respective positions of the material to be tested, the pixel corresponding to the detected candidate flaw position having a gray level capable of being identified from the other pixels, in correspondence to a phase of the candidate flaw signal in the candidate flaw position; a continuity evaluating device evaluating a continuity of the candidate flaw position with regard to a direction corresponding to a phase of the candidate flaw signal at the candidate flaw position existing in each of the testing images, by individually applying an image processing to each of the testing images; and a flaw detecting device detecting the flaw based on the continuity of the candidate flaw position.

Preferably, in the magnetic testing apparatus, frequencies of the first current and the second current satisfy the following equation (1).

$$\text{frequency of first current/frequency of second current} \geq 8 \quad (1)$$

In accordance with the present invention, it is possible to solve the problems (1) to (4) mentioned above, and to precisely detect the flaws extending in the various directions and existing in the material to be tested, by using the rotating magnetic field.

BRIEF DESCRIPTION OF THE DRAWINGS

FIGS. 16A and 16B are explanatory views describing an outline of a testing in accordance with an example of the present invention, in which FIG. 16A shows a longitudinal sectional view, and FIG. 16B is a plan view.

DESCRIPTION OF THE PREFERRED EMBODIMENTS

A description will be given below of an embodiment in accordance with the present invention appropriately with reference to the accompanying drawings.

Figure 9:
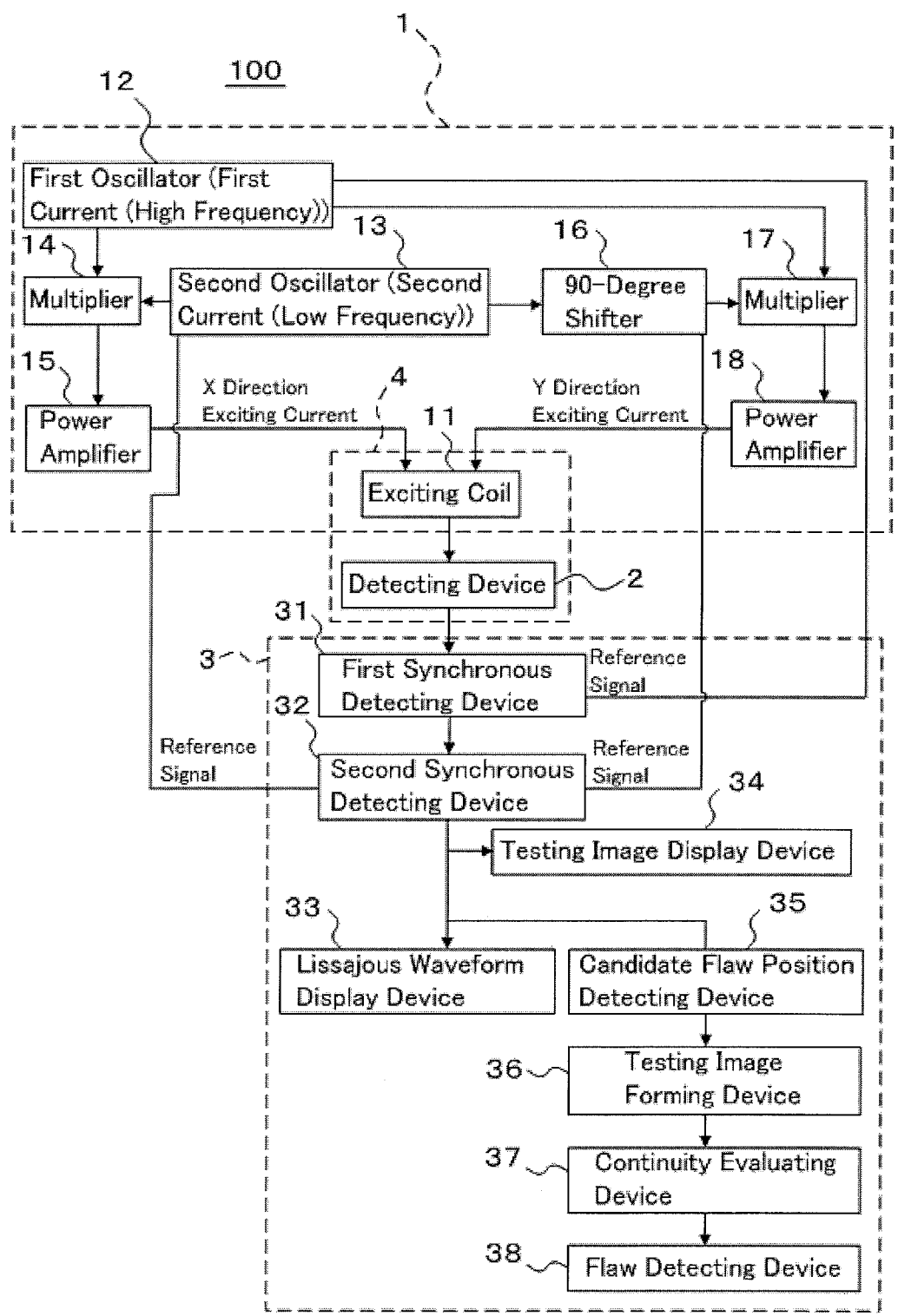
FIG. 9 is a block diagram showing a schematic configuration of a magnetic testing apparatus in accordance with an embodiment of the present invention.
Figure 10:
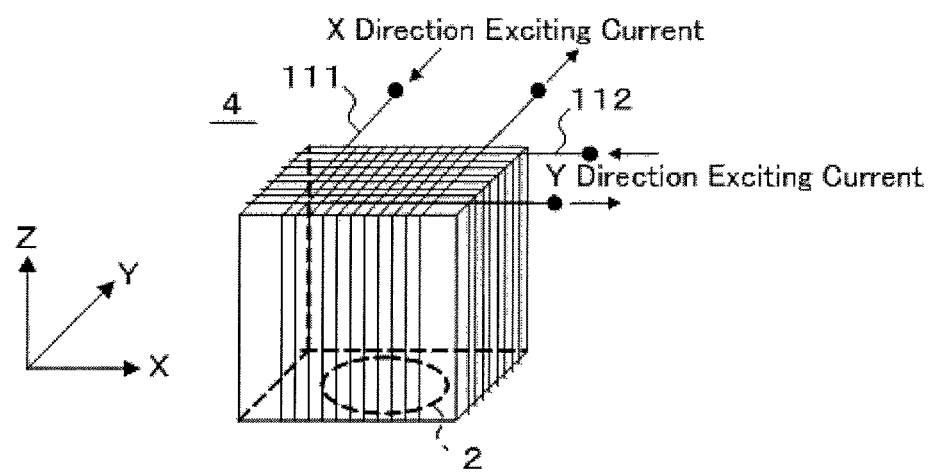
FIG. 10 shows a schematic outer appearance view of a testing probe shown in FIG. 9.

FIG. 9 is a block diagram showing a schematic configuration of a magnetic testing apparatus in accordance with an embodiment of the present invention. FIG. 10 shows a schematic outer appearance view of a testing probe shown in FIG. 9. As shown in FIG. 9, a magnetic testing apparatus 100 in accordance with the present embodiment is provided with a magnetizing device 1 applying a rotating magnetic field to a material to be tested, a detecting device 2 detecting a testing signal generated by the rotating magnetic field, and a signal processing device 3 applying a signal processing to the testing signal.

The magnetizing device 1 is provided with an exciting coil 11 applying an exciting current for generating the rotating magnetic field. As shown in FIG. 10, the exciting coil 11 is provided with an X-direction exciting coil 111 and a Y-direction exciting coil 112 which are arranged such that winding directions of lead wires are orthogonal to each other, and center positions coincide with each other. The magnetic field is generated in an X direction shown in FIG. 10, by applying the exciting current (the X-direction exciting current) to the X-direction exciting coil 111. On the other hand, the magnetic field is generated in a Y direction shown in FIG. 10, by applying the exciting current (the Y-direction exciting current) to the Y-direction exciting coil 112. Further, a resultant magnetic field of the magnetic fields generated by the respective exciting coils 111 and 112 is rotated by 360 degrees around the center position of each of the exciting coils 111 and 112, by shifting phases of the alternating exciting currents applied to the exciting coils 111 and 112 by 90 degrees.

The exciting coil 11 in accordance with the present embodiment is characterized by a point that an alternating current obtained by superimposing a first current and a second current having a lower frequency than the first current is applied as the exciting current. Specifically, the X-direction exciting current obtained by superimposing the first current and the second current is applied to the X-direction exciting coil 111, and the Y-direction exciting current is applied to the Y-direction exciting coil 112, the Y-direction exciting current being structured such that the first current and the second current are superimposed, and the phase is shifted by 90 degrees with respect to the X-direction exciting current. A description will be more specifically given below of the feature portion mentioned above appropriately with reference to FIGS. 11A and 11B.

Figure 11A:
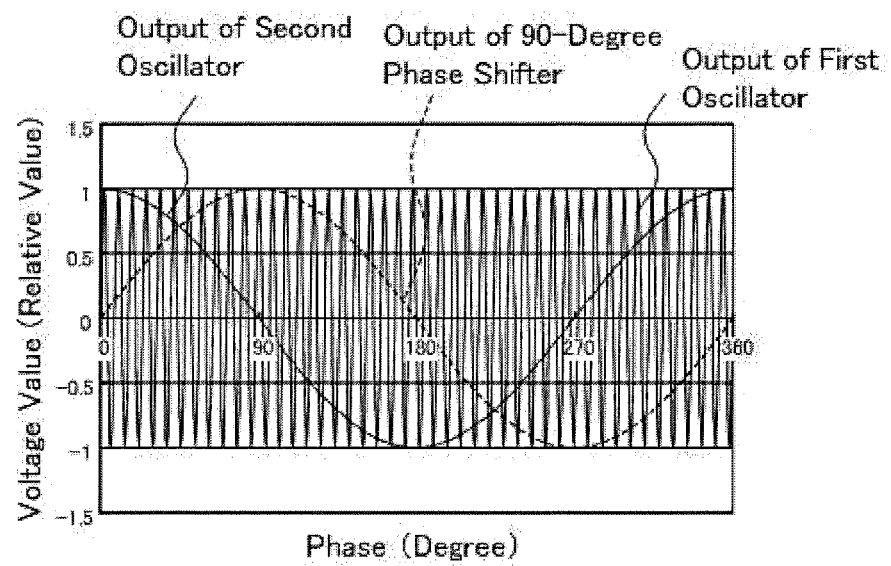
FIGS. 11A and 11B are graphs showing a signal waveform generated by a magnetizing device shown in FIG. 9.

The magnetizing device 1 in accordance with the present embodiment is provided with a first oscillator 12 generating a voltage waveform of the first current, and a second oscillator 13 generating a voltage waveform of the second current. In other words, as shown in FIG. 11A, the voltage waveform (hereinafter, refer to as a first voltage waveform) having the same frequency as the previously decided frequency of the first current is output from the first oscillator 12, and the voltage waveform (hereinafter, refer to as a second voltage waveform) having the same frequency as the previously decided frequency of the second current is output from the second oscillator 13. The frequency of the second voltage waveform is lower than the frequency of the first voltage waveform. In this case, a ratio between the previously decided frequency of the first current and the previously decided frequency of the second current may be appropriately decided based on what resolution an angle information of the flaw is estimated, however, is preferably decided in such a manner as to satisfy a relation the frequency of the first current/the frequency of the second current$\geq 8$.

Figure 11B:
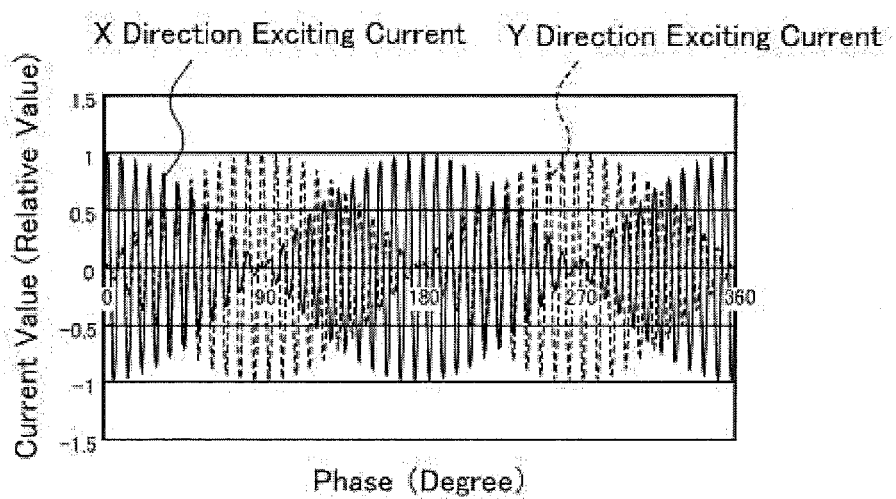

Further, the magnetizing device 1 is provided with a multiplier 14, and a power amplifier 15. The first voltage waveform output from the first oscillator 12 and the second voltage waveform output from the second oscillator 13 are multiplied (superimposed) by the multiplier 14, and is converted into a current by the power amplifier 15. The current output from the power amplifier 15 is used as the X-direction exciting current applied to the X-direction exciting coil 111, as shown in FIG. 11B.

On the other hand, the magnetizing device 1 is provided with a 90-degree phase shifter 16, a multiplier 17, and a power amplifier 18. The second voltage waveform output from the second oscillator 13 is shifted its phase by 90 degrees by the 90-degree phase shifter 16. For example, in the case that the second voltage waveform output from the second oscillator 13 is a cosine wave, as shown in FIG. 11A, the voltage waveform output from the 90-degree phase shifter 16 comes to a sine wave having the same frequency as the second voltage waveform. Further, the first voltage waveform output from the first oscillator 12 and the voltage waveform output from the 90-degree phase shifter 16 are multiplied (superimposed) by the multiplier 17, and is converted into the current by the power amplifier 18. The current output from the power amplifier 18 is used as the Y-direction exciting current applied to the Y-direction exciting coil 112, as shown in FIG. 11B.

In accordance with the structure mentioned above, as shown in FIG. 11B, the X-direction exciting current obtained by superimposing the first current and the second current is applied to the X-direction exciting coil 111, and the Y-direction exciting current is applied to the Y-direction exciting coil 112, the Y-direction exciting current being structured such that the first current and the second current are superimposed, and the phase is shifted by 90 degrees with respect to the X-direction exciting current.

As mentioned above, since the magnetizing device 1 in accordance with the present embodiment uses the alternating current obtained by the superimposing the first current and the second current having the lower frequency than the first current as the exciting current (the X-direction exciting current and the Y-direction exciting current) for exciting the rotating magnetic field, the magnetic field generated by the first current having the higher frequency (and an eddy current induced by the magnetic field) are applies predominantly to the material to be tested, and the second current having the low frequency mainly functions for rotating the direction of the generated magnetic field (and the eddy current) in the material to be tested.

The detecting device 2 in accordance with the present embodiment is constructed as a detection coil for detecting a change of the magnetic flux in a Z direction (see FIG. 10) which is orthogonal to the X direction and the Y direction while passing through a center of the exciting coil 11. The detection coil 2 detects the change of the magnetic flux in the Z direction so as to output as a testing signal to the signal processing device 3. In this case, the detection coil 2 is integrated with the X-direction exciting coil 111 and the Y-direction exciting coil 112 mentioned above so as to form a testing probe 4.

The signal processing device 3 is provided with a first synchronous detecting device 31 synchronously detecting the testing signal detected by the detecting device 2 by using the first current as a reference signal. Specifically, the first synchronous detecting device 31 synchronously detects the testing signal output from the detecting device 2 by using the first voltage waveform (the voltage waveform of the first current) output from the first oscillator 12 as the reference signal. Further, the first synchronous detecting device 31 smoothens an alternating current extracted by the synchronous detection per unit region corresponding to about two or three cycles of the reference signal (the voltage waveform of the first current) so as to output.

Figure 1:
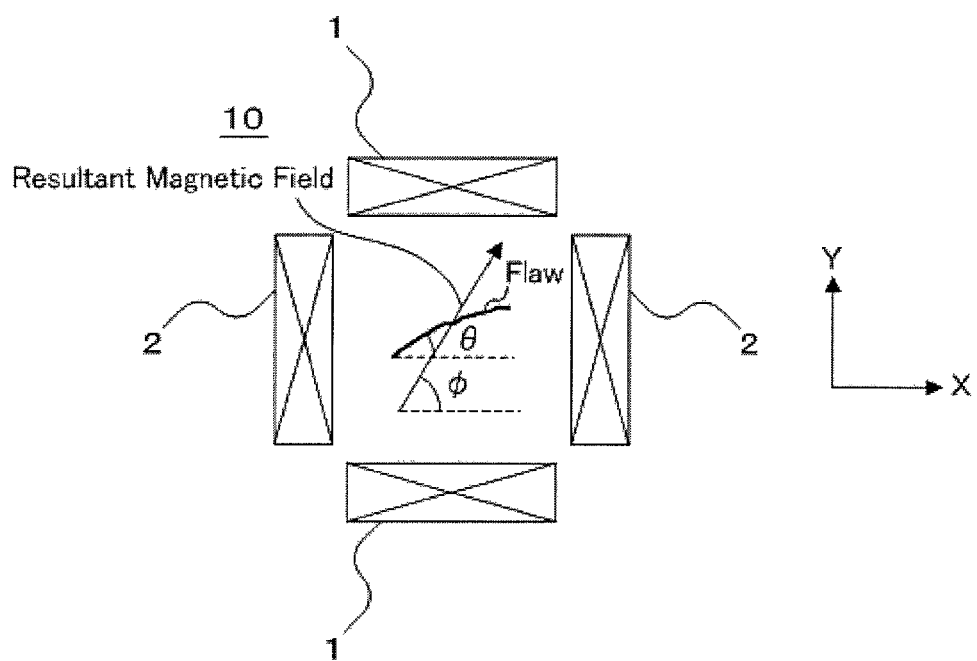
FIG. 1 is a plan cross-sectional view showing an example of an exciting coil for generating a rotating magnetic field.
Figure 2A:
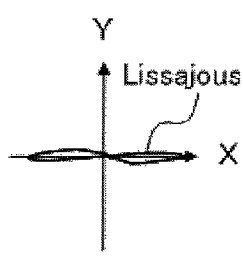
FIG. 2 is a schematic diagram showing an example of a Lissajous waveform.
Figure 2B:
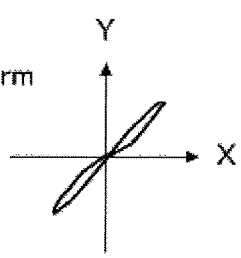
Figure 2C:
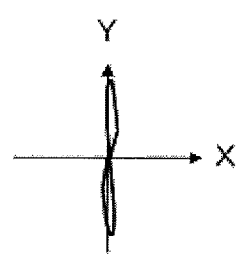
Figure 3A:
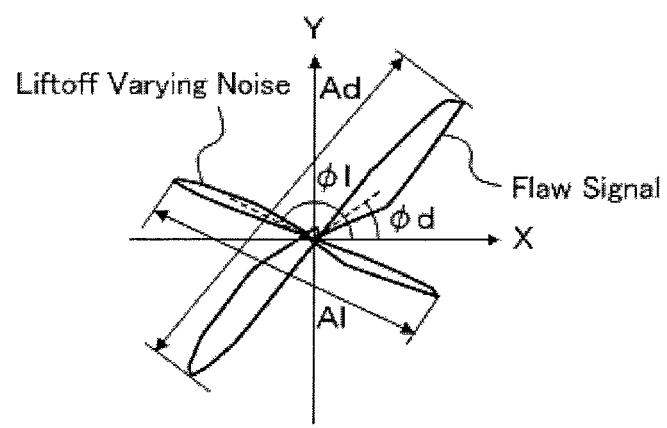
FIGS. 3A and 3B are schematic views of a Lissajous waveform indicating a fact that a flaw signal and a liftoff varying noise have a phase difference.
Figure 3B:
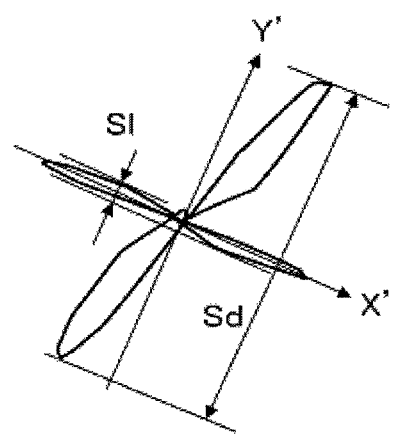
Figure 4:
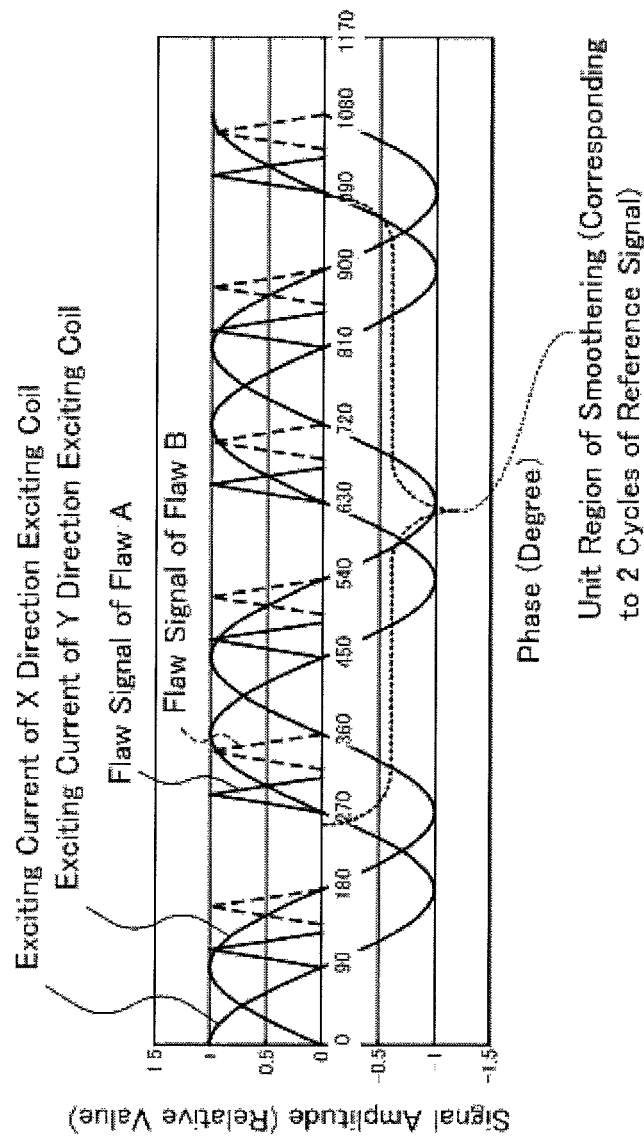
FIG. 4 is a graph showing a time sequence relation between a exciting current waveform and a flaw signal waveform in a conventional magnetic testing method utilizing the rotating magnetic field.
Figure 5A:
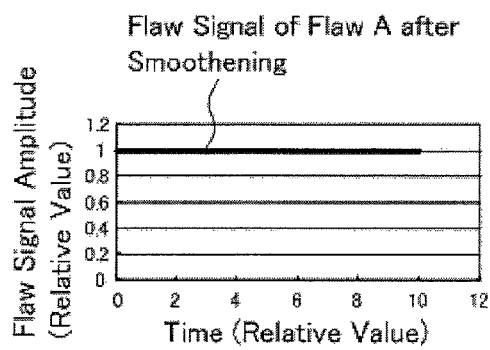
FIGS. 5A and 5B are graphs each showing a flaw signal waveform after synchronously detecting a testing signal including the flaw signal by using a exciting current shown in FIG. 4 as a reference signal, and smoothening the flaw signal extracted by the synchronous detection per unit region corresponding to two cycles of the reference signal.
Figure 5B:
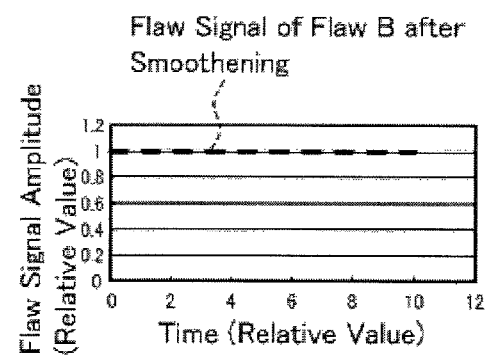

In this case, in the same manner as mentioned above about the related art, it is assumed that two kinds of flaws A and B (an angle θ (see FIG. 1) of the flaw A equals to 20 degrees, and an angle θ of the flaw B equals to 70 degrees) having different extending directions exist in the material to be tested, and α equals to 20 degrees. In the present invention, in the case of the magnetic flux leakage testing method, a flaw signal of the flaw A becomes maximum in the case that a direction φ (see FIG. 1) of the magnetic field satisfies a relation φ=20 degrees+90 degrees+180 degrees×n (n is an integral number) under the assumption mentioned above, and an amplitude comes to 0 if it goes beyond a range φ±20 degrees. In the same manner, a flaw signal of the flaw B becomes maximum in the case that the direction φ of the magnetic field satisfies a relation φ=70 degrees+90 degrees+180 degrees×n (n is an integral number), and the amplitude comes to 0 if it goes beyond the range φ±20 degrees.

Figure 12:
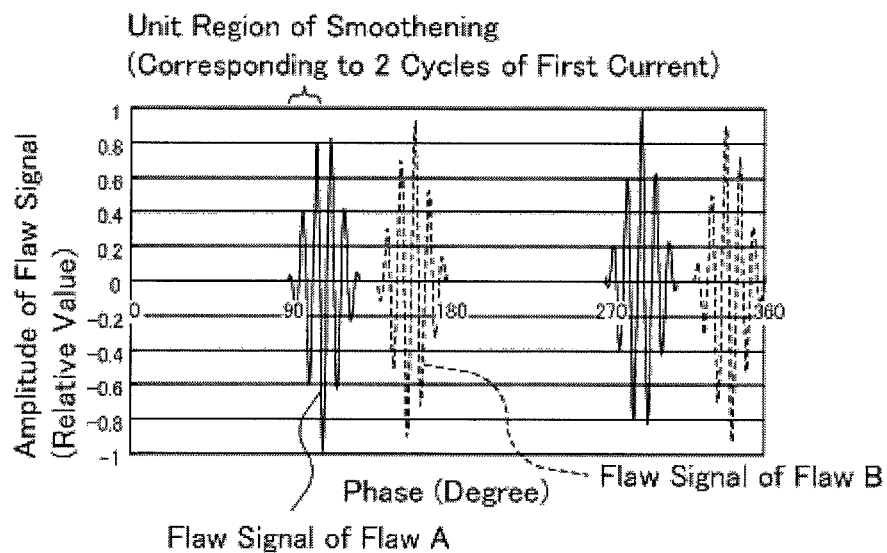
FIG. 12 is a graph schematically showing an example of a flaw signal waveform detected by a detecting device shown in FIG. 9.
Figure 13:
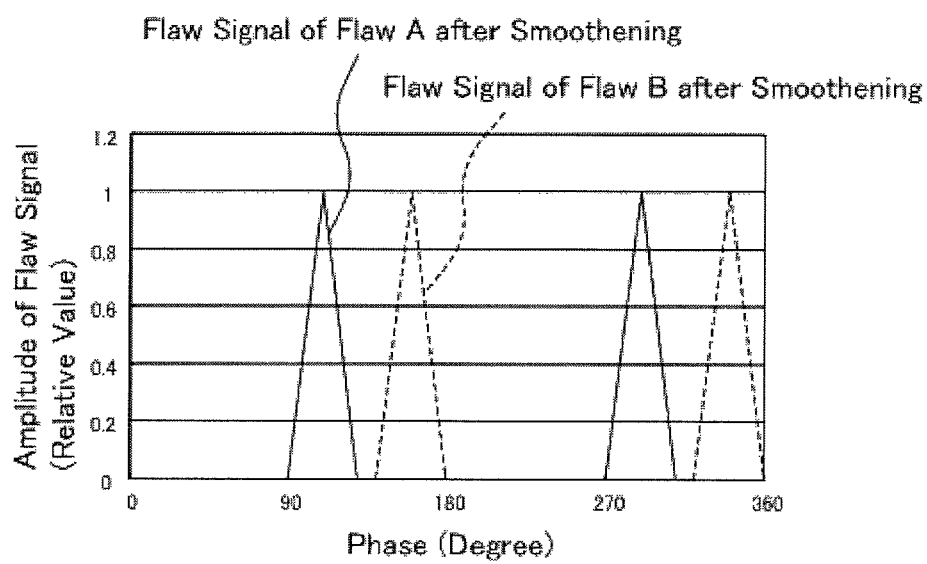
FIG. 13 is a graph schematically showing one example of a flaw signal waveform after synchronously detecting the testing signal including the flaw signal by using a first current as a reference signal in the first synchronous detecting device shown in FIG. 9, and smoothening a flaw signal extracted by the synchronous detection per unit region corresponding to two cycles of the reference signal.

FIG. 12 is a graph schematically showing the flaw signal waveforms of the flaws A and B under the assumption mentioned above. Further, FIG. 13 is a graph showing a flaw signal waveform after synchronously detecting the testing signal including the flaw signal by using the first current as the reference signal in the first synchronous detecting device, and smoothening the flaw signal extracted by the synchronous detection per unit region corresponding to two cycles of the reference signal. A waveform of a noise included in the testing signal is not given in FIGS. 12 and 13.

As is known by referring to the FIG. 12 and FIGS. 11A and 11B mentioned above, since a cycle component coinciding with a cycle of the first current is included in the flaw signal obtained from the flaws A and B, it is possible to extract the flaw signal at a high S/N ratio from the testing signal, in comparison with the conventional case of synchronously detecting by a reference signal (corresponding to the second current in the present invention) having the same frequency as the rotating frequency of the magnetic field, by synchronously detecting by using the first current as the reference signal.

Further, as shown in FIG. 13, since the phase information of the flaw signal after smoothening can be held, even by smoothening the flaw signal extracted by synchronously detecting by using the first current as the reference signal per unit region corresponding to two cycles of the reference signal, it is possible to estimate the angle information of the flaws A and B (what directions they extend in).

The signal processing device 3 is provided with a second synchronous detecting device 32 extracting a candidate flaw signal by synchronously detecting the output signal of the first synchronous detecting device 31 by using the second current as the reference signal. Further, the signal processing device 3 is provided with a Lissajous waveform display device 33 displaying a Lissajous waveform based on the output signal of the second synchronous detecting device 32.

Specifically, the second synchronous detecting device 32 branches the output signal of the first synchronous detecting device 31 into two signals which are identical to each other. Further, the second synchronous detecting device 32 synchronously detects one of the branched signals by using the second voltage waveform (the voltage waveform of the second current) output from the second oscillator 13 as the reference signal. The synchronously detected signal (the X signal) is output to the Lissajous waveform display device 33. Further, the second synchronous detecting device 32 synchronously detects the other of the branched signals by using the voltage waveform (the voltage waveform in which the phase is different by 90 degrees from the voltage waveform of the second current) output from the 90-degree phase shifter 16 as the reference signal. The synchronously detected signal (the Y signal) is output to the Lissajous waveform display device 33.

The Lissajous waveform display device 33 displays the Lissajous waveform in which the X signal output from the second synchronous detecting device 32 is set to an X-axis component, and the Y signal is set to a Y-axis component. At this time, it is possible to improve the S/N ratio by rotating the X-Y coordinate system in such a manner that the liftoff varying noise of the detection coil 2 is along the X axis as occasion demands. Since the phase information of the flaw signal after being smoothened by the first synchronous detecting device 31 is held as mentioned above, it is possible to apply the phase analysis method as mentioned above, by the second synchronous detecting device 32 and the Lissajous waveform display device 33, and it is possible to suppress an influence of the liftoff varying noise with respect to the flaw detection performance.

Further, the signal processing device 3 is provided with a testing image display device 34 displaying a testing image constructed by a plurality of pixels corresponding to respective positions of the material to be tested, the testing image being structured such that each of the pixels has a gray level corresponding to an intensity of the candidate flaw signal at each of the positions, and a phase of the candidate flaw signal at each of the positions can be identified.

Specifically, the testing image display device 34 calculates an amplitude A expressed by the following equation (2) and a phase θ expressed by the following equation (3), based on an intensity X of the X signal and an intensity Y of the Y signal which are output from the second synchronous detecting device 32.

$$A = (x^2 + y^2)^{1/2} \quad (2)$$

$$\theta = \tan^{-1}(Y/X) \quad (3)$$

Further, a relative positional relationship between the testing probe 4 and the material to be tested detected by an appropriate sensor (not shown) (i.e., a position of the material tested by the testing probe 4) is input to the testing image display device 34. The testing image display device 34 displays a testing image constructed by a plurality of pixels corresponding to respective positions of the material to be tested detected by the sensor, and structured such that each of the pixels has a gray level corresponding to the amplitude A in each of the positions and the phase θ in each of the positions can be identified. For example, the testing image display device 34 displays one color image in which the pixels are colored into different colors in correspondence to the phase θ (the gray level of each of the pixels is different in correspondence to the amplitude A) as the testing image. Alternatively, the testing display device 34 displays a plurality of gray images (the gray level of each of the pixels is different in correspondence to the amplitude A) in which the phase θ (range of the phase θ) included in each of the images is different, as the testing image.

Since the signal processing device 3 is provided with the testing image display device 34 having the structure mentioned above, it is possible to visually observe the phase (the angle information) in addition to the amplitude A in the testing image. Accordingly, it is possible to accurately evaluate the continuity of the flaw.

In the present embodiment, the description is given of the structure in which each of the pixels of the testing image displayed by the testing image display device 34 has the gray level corresponding to the amplitude A in each of the positions of the material to be tested. However, the present invention is not limited thereto, but it is possible to employ a structure in which each of the pixels of the testing image displayed by the testing image display device 34 has a gray level corresponding to an intensity X of the X signal or an intensity Y of the Y signal in each of the positions of the material to be tested. Further, it is possible to employ a structure in which each of the pixels of the testing image displayed by the testing image display device 34 has a gray level corresponding to an intensity of a signal component in a Y'-axis direction in an X'-Y' coordinate system after rotating the X-Y coordinate system in such a manner that the liftoff varying noise of the detection coil 2 is along the X axis. Further, it is possible to employ a structure in which each of the pixels of the testing image displayed by the testing image display device 34 has a gray level obtained by binarizing any one of the amplitude A, the intensity of the X signal, the intensity of the Y signal and the intensity of the signal component in the Y'-axis direction by a predetermined threshold value.

Further, the signal processing device 3 is provided with a candidate flaw position detecting device 35 detecting a candidate flaw position in the material to be tested by binarizing the candidate flaw signal by a predetermined threshold value, a testing image forming device 36 forming a plurality of testing images which are constructed by a plurality of pixels corresponding to the respective positions of the material to be tested and have such a gray level that the pixel corresponding to the detected candidate flaw position can be identified from the other pixels, in correspondence to the phase of the candidate flaw signal in the candidate flaw position, a continuity evaluating device 37 evaluating a continuity of the candidate flaw position with regard to a direction corresponding to the phase of the candidate flaw signal in the candidate flaw position existing in each of a plurality of testing images, by individually applying an image processing to each of the testing images, and a flaw detecting device 38 detecting the flaw based on the continuity of the candidate flaw position.

Specifically, the candidate flaw position detecting device 35 calculates the amplitude A expressed by the following equation (2) and the phase θ expressed by the equation (3), based on the intensity X of the X signal and the intensity Y of the Y signal which are output from the second synchronous detecting device 32.

$$A=(X^2+y^2)^{1/2} \tag{2}$$

$$\theta=\tan^{-1}(Y/X) \tag{3}$$

The candidate flaw position detecting device 35 detects the candidate flaw position in the material to be tested so as to output as the candidate flaw position detection signal to the testing image forming device 36, by binarizing the amplitude A by a predetermined threshold value. Further, the candidate flaw position detecting device 35 outputs the phase θ corresponding to the candidate flaw position detection signal to the testing image forming device 36.

Figure 6:
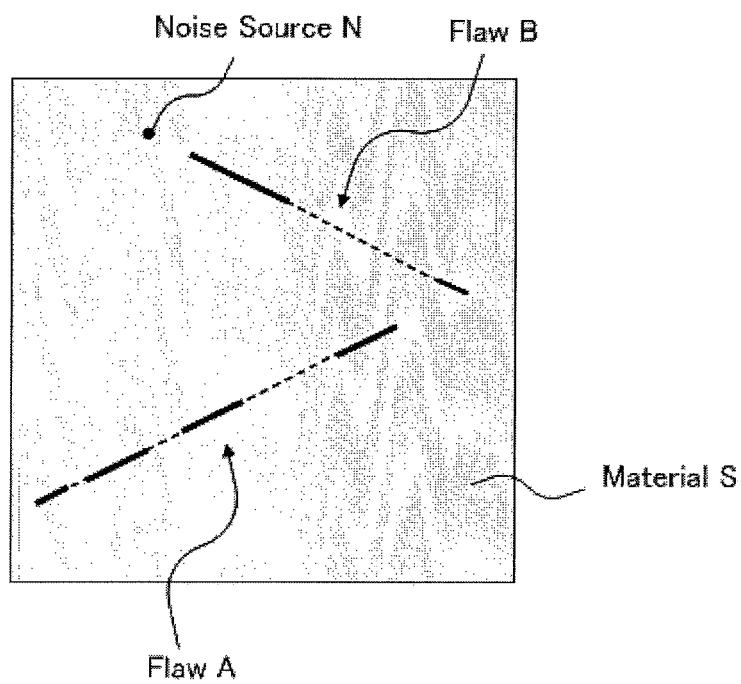
FIG. 6 is a diagram schematically showing a flaw and a noise source existing in the material to be tested.
Figure 7:
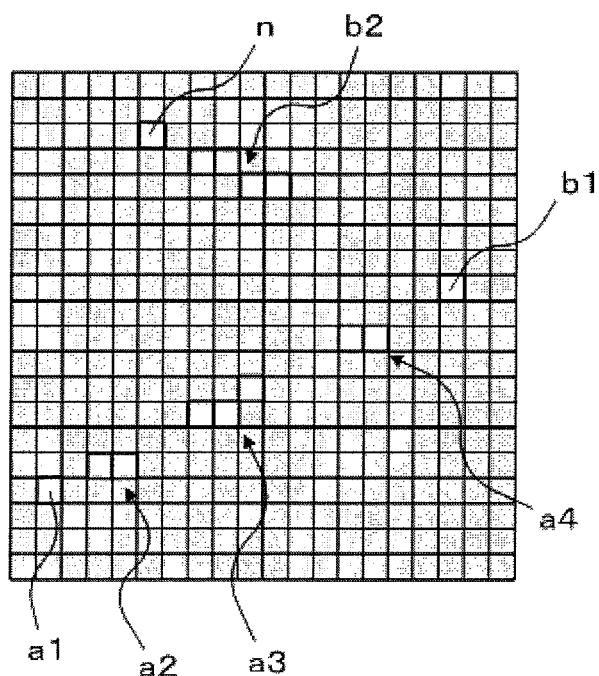
FIG. 7 is a diagram schematically showing an example of a conventional testing image obtained with regard to the material to be tested shown in FIG. 6.
Figure 8:
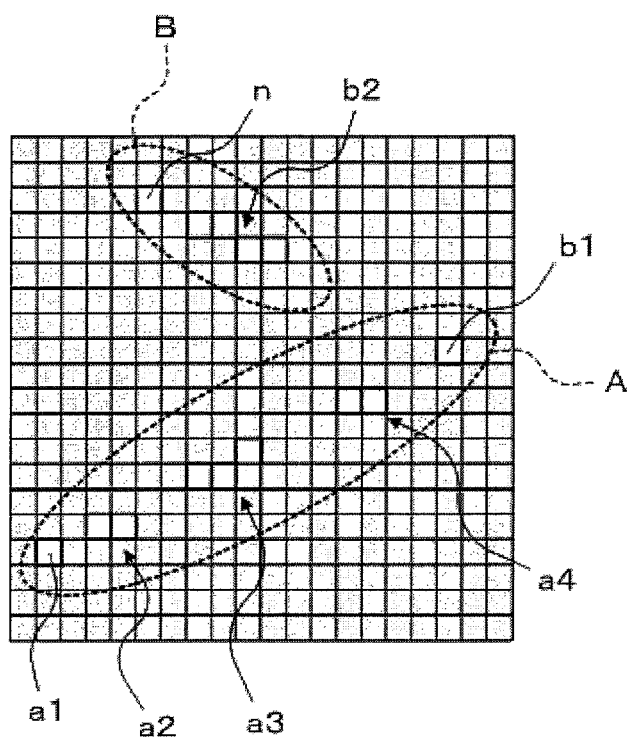
FIG. 8 is a diagram showing a result obtained by evaluating a continuity of the flaw with respect to the testing image shown in FIG. 7.

To the testing image forming device 36, there are input the candidate flaw position detection signal output from the candidate flaw position detecting device 35, and the relative positional relationship (that is, the position of the material to be tested where the flaw detection is carried out by the testing probe 4) between the testing probe 4 and the material to be tested which is detected by an appropriate sensor (not shown). The testing image forming device 36 forms a plurality of testing images which are constructed by a plurality of pixels corresponding to the respective positions of the material to be tested detected by the sensor, and have such a gray level that the pixel corresponding to the detected candidate flaw position can be identified from the other pixels (for example, the pixel corresponding to the detected candidate flaw position has a gray level of 255, and the other pixels have a gray level of 0), in correspondence to the phase θ (the range of phase) in the candidate flaw position. For example, the testing image forming device 36 forms two testing images in which the ranges of the phases θ in the candidate flaw positions are respectively 0 degrees≦θ<45 degrees and 135 degrees≦θ<180 degrees. FIGS. 14A and 14B are views schematically showing one example of the testing image formed by the testing image forming device 36, with respect to the material S shown in FIG. 6 mentioned above, in which FIG. 14A shows the testing image in which the range of the phase θ in the candidate flaw position is 0 degrees≦θ<45 degrees, and FIG. 14B shows the testing image in which the range of the phase θ in the candidate flaw position is 135 degrees≦θ<180 degrees. Four pixel groups a1 to a4 corresponding to the flaw A are accurately included as the candidate flaw position in the testing image shown in FIG. 14A, and two pixel groups b1 and b2 corresponding to the flaw B are accurately included as the candidate flaw position in the testing image shown in FIG. 14B. In this case, since the candidate flaw position corresponding to the noise source N has the phase θ in 45 degrees≦θ<135 degrees, the testing image is not formed. However, the present invention is not limited thereto, but it is possible to determine whether or not it is a flaw, in correspondence to a magnitude of the flaw length calculated by the image processing by the continuity evaluating device 37 as mentioned below, by forming one or a plurality of testing images having different ranges of the phase θ, with respect to the candidate flaw position having the phase θ in 45 degrees≦θ<135 degrees.

Figure 14A:
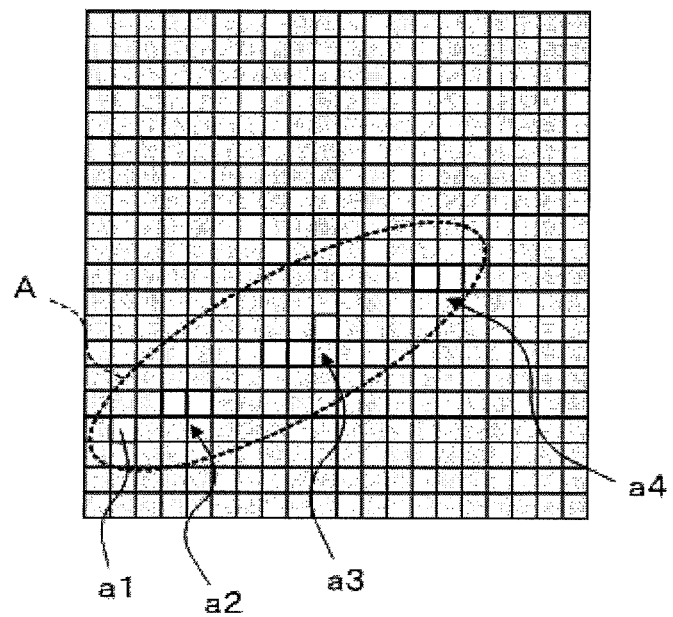
FIGS. 14A and 14B are views schematically showing one example of a testing image formed by the testing image forming device shown in FIG. 9, with respect to the material to be tested shown in FIG. 6.
Figure 14B:
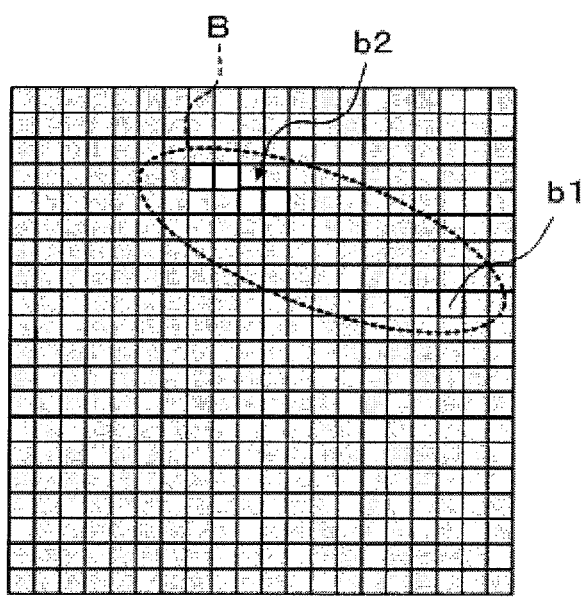
Figure 15A:
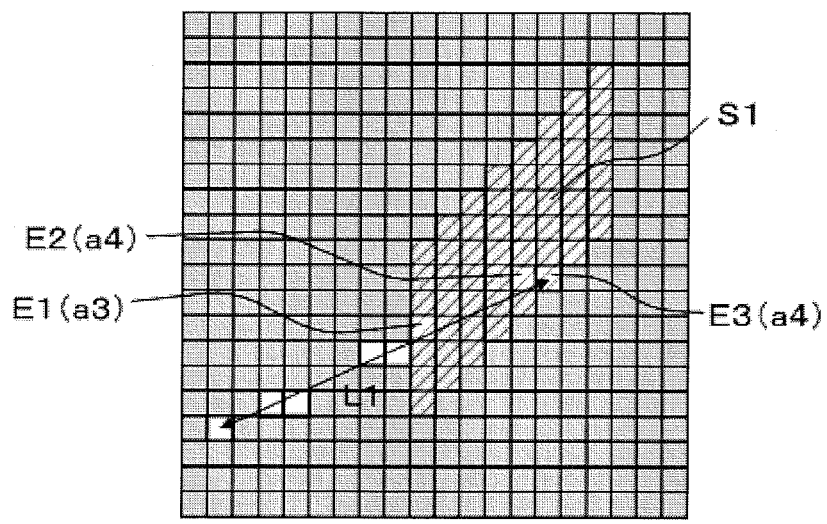
FIGS. 15A and 15B are diagrams describing an evaluating method carried out by a continuity evaluating device shown in FIG. 9, with regard to the testing image shown in FIGS. 14A and 14B.
Figure 15B:
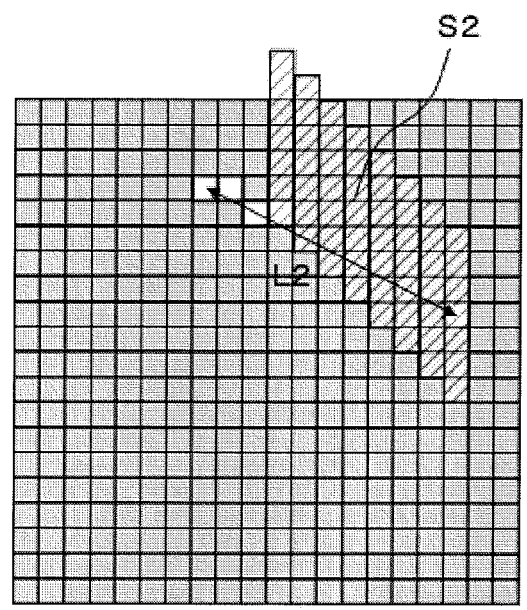

The continuity evaluating device 37 evaluates the continuity of the candidate flaw position with regard to the direction corresponding to the phase θ in the candidate flaw position existing in each of the two testing images, for example, by individually applying the image processing to each of the testing images shown in FIGS. 14A and 14B. The evaluation of the continuity employs an appropriate image processing filter. For example, with regard to the testing image shown in FIG. 14A, it is determined whether or not the other pixels constructing the candidate flaw position exist within a vicinity pixel region (a hatched region S1 in the figure) corresponding to the range (0 degrees≦θ<45 degrees) of the phase θ, with regard to one remarked pixel E1 constructing the candidate flaw position, as shown in FIG. 15A. If the other pixel exists, it is determined that the other pixel and the remarked pixel E1 are in the pixel region about the same candidate flaw position. In the example shown in FIG. 15A, the remarked pixel E1 and the other pixels E2 and E3 are determined to be in the pixel region about the same candidate flaw position. The continuity evaluating device 37 repeatedly carries out the process mentioned above by using all the pixels constructing the candidate flaw position within each of the testing images as the remarked pixel, and as a result, calculates the length of the one which is determined to be the same candidate flaw position. In the example shown in FIG. 15A, it is determined that all the pixels constructing the candidate flaw position are the same candidate flaw position, and its length L1 (a distance between both end pixels constructing the same candidate flaw position) is calculated. With regard to the testing image shown in FIG. 14B, the same process is carried out as shown in FIG. 15B, and a length L2 of the candidate flaw position is calculated. In this case, since the range (135 degrees≦θ<180 degrees) of the phase θ in the testing image shown in FIG. 14B is different from the range (0 degrees≦θ<45 degrees) of the phase θ in the testing image shown in FIG. 14A, a vicinity pixel region (a hatched region S2 in the figure) shown in FIG. 15B is different from the vicinity pixel region shown in FIG. 15A.

The flaw detecting device 38 detects the flaw based on the continuity of the candidate flaw position. In other words, for example, in the case that the length of the candidate flaw position calculated by the continuity evaluating device 37 is longer than a predetermined length, it is determined that it is a flaw, and in the case that it is equal to or shorter than the predetermined length, it is determined that it is not a flaw. In the case that the length L1 of the candidate flaw position shown in FIG. 15A, and the length L2 of the candidate flaw position shown in FIG. 15B are longer than the predetermined length, both of them are detected as a flaw. Further, the candidate flaw position existing in the range of the phase θ in which the testing image is not formed is determined as the position corresponding to the noise source.

Since the signal processing device 3 is provided with the candidate flaw position detecting device 35, the testing image forming device 36, the continuity evaluating device 37 and the flaw detecting device 38 which have the structure mentioned above, it is possible to automatically and accurately evaluate the continuity of the flaw by utilizing the phase (the angle information) in addition to the amplitude A in the testing image.

In the present embodiment, the description is given of the structure in which the candidate flaw position detecting device 35 binarizes the amplitude A by the predetermined threshold value, thereby detecting the candidate flaw position in the material to be tested so as to output as the candidate flaw position detection signal to the testing image forming device 36. However, the present invention is not limited thereto, but can employ such a structure that the candidate flaw position detecting device 35 binarizes the intensity X of the X signal or the intensity Y of the Y signal by the predetermined threshold value, thereby detecting the candidate flaw position in the material to be tested so as to output as the candidate flaw position detection signal to the testing image forming device 36. Further, it is possible to employ such a structure that the candidate flaw position detecting device 35 detects the candidate flaw position in the material to be tested by binarizing the intensity of the signal component in the Y'-axis direction in the X'-Y' coordinate system after rotating the X-Y coordinate system in such a manner that the liftoff varying noise of the detection coil 2 is along the X axis by a predetermined threshold value, thereby outputting as the candidate flaw position detection signal to the testing image forming device 36.

As described above, in accordance with the magnetic testing apparatus 100 of the present embodiment, it is possible to solve the problem of the conventional magnetic testing method utilizing the rotating magnetic field caused by using the exciting current having the single frequency, and to precisely detect the flaws extending in the various directions and existing in the material to be tested by using the rotating magnetic field.

The feature of the present invention will be further clarified below by showing the examples.

Figure 16A:
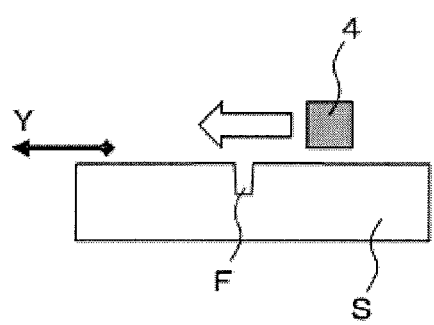
Figure 16B:
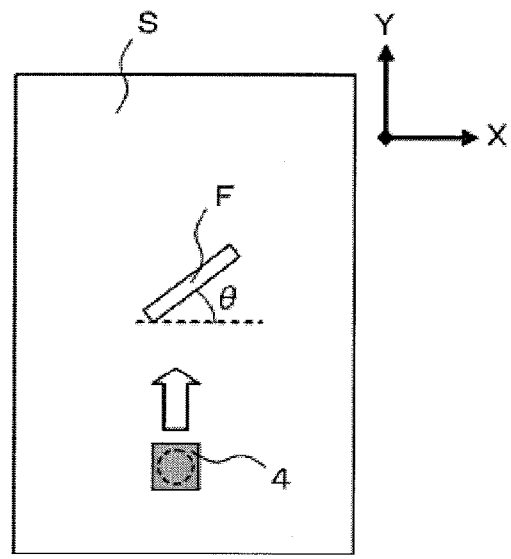

A testing of a linear artificial flaw F formed in a steel plate S is carried out, as shown in FIGS. 16A and 16B, by using the magnetic testing apparatus 100 an outline structure of which is shown in FIGS. 9 and 10. An outline of a testing condition is shown in Table 1, and an outline specification of the material to be tested is shown in Table 2. As shown in Table 1, there is manufactured a testing probe 4 provided with X-direction and Y-direction exciting coils each of which is wound at 50 turns around side faces of a core material corresponding to a cube in which one side is 6 mm, and a detecting coil which is attached to a bottom face of the core material, has a diameter 5 mm and is wound at 100 turns.

TABLE 1

| | |
|---|---|
| X-direction exciting coil | 6 mm square, 50 turns |
| Y-direction exciting coil | 6 mm square, 50 turns |
| Detection coil | 5 mm $\phi$, 100 turns |
| Detection coil liftoff | 0.5 mm |
| Exciting current value (pulse height value) | 1.0 $A_{0-P}$ |
| Frequency of first current | 20 kHz |
| Frequency of second current | 100 Hz |

TABLE 2

| | |
|---|---|
| Material of steel plate | S45C |
| Dimension of steel plate | Thickness 10 mm, width 30 mm, length 150 mm |
| Dimension of artificial flaw | Depth 1.0 mm, width 0.5 mm, length 20 mm |

Further, as shown in FIGS. 16A and 16B, a testing signal is detected by scanning the manufactured testing probe 4 in a certain direction (a Y direction shown in FIGS. 16A and 16B) in such a manner as to pass just above the steel plate S and just above the artificial flaw F. At this time, the testing signal is detected per each of the angles by sequentially changing the relative angle between the direction in which the artificial flaw extends and the scanning direction of the testing probe 4. Specifically, in the case that the angle formed by an X direction shown in FIGS. 16A and 16B and the direction in which the artificial flaw F extends is set to θ, the testing signal is detected per each of the angles θ by changing a range of θ=0 degrees to 75 degrees at a pitch of 15 degrees.

Figure 17:
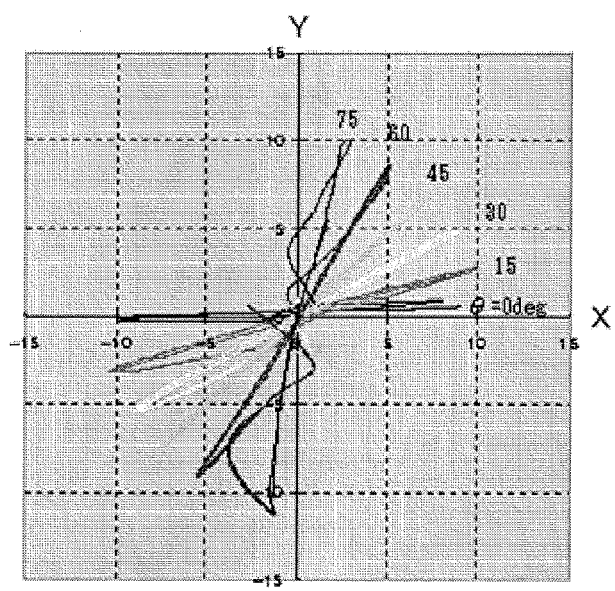
FIG. 17 shows a Lissajous waveform of a flaw signal obtained by the testing shown in FIG. 16.

FIG. 17 shows a Lissajous waveform of the flaw signal obtained by the testing mentioned above. As shown in FIG. 17, it is possible to identify that the Lissajous waveform of the flaw signal at each of the angles (θ=0 degrees, 15 degrees, 30 degrees, 45 degrees, 60 degrees, 75 degrees) has a phase which is different from each other. Further, the Lissajous waveform of the flaw signals have all sufficiently large amplitudes with respect to the flaw in any angle. As a result, in accordance with the present invention, there can be known that it is possible to sufficiently obtain the effect of the synchronous wave detection, and to estimate the angle information of the flaw. Accordingly, it is possible to accurately evaluate the continuity of the flaw by using the testing image.

In the embodiment shown in FIGS. 11A and 11B, the liftoff varying noise is not generated, however, in the case that it is generated, it is possible to suppress the influence of the liftoff varying noise with respect to the flaw detection performance by rotating the X-Y coordinate system in such a manner that the liftoff varying noise is along the X axis, and setting the signal component in the Y'-axis direction in the X'-Y' coordinate system after the rotation to the candidate flaw signal.

What is claimed is:

1. A magnetic testing method applying a rotating magnetic field to a material to be tested and detecting a flaw based on a testing signal generated by the rotating magnetic field, the method comprising the steps of:

extracting a candidate flaw signal by using an alternating current obtained by superimposing a first current and a second current having a lower frequency than the first current, as an exciting current for exciting the rotating magnetic field, synchronously detecting the testing signal by using the first current as a reference signal, and thereafter synchronously detecting by using the second current as a reference signal;

displaying a testing image constructed by a plurality of pixels corresponding to respective positions of the material to be tested, each of the pixels having a gray level corresponding to an intensity of the candidate flaw signal at each of the positions, and a phase of the candidate flaw signal at each of the positions in the testing image being capable of being identified; and detecting the flaw based on the displayed testing image.

2. A magnetic testing method applying a rotating magnetic field to a material to be tested and detecting a flaw based on a testing signal generated by the rotating magnetic field, the method comprising the steps of:

extracting a candidate flaw signal by using an alternating current obtained by superimposing a first current and a second current having a lower frequency than the first current, as an exciting current for exciting the rotating magnetic field, synchronously detecting the testing signal by using the first current as a reference signal, and thereafter synchronously detecting by using the second current as a reference signal;

detecting a candidate flaw position in the material to be tested by binarizing the candidate flaw signal by a predetermined threshold value;

forming a plurality of testing images which are constructed by a plurality of pixels corresponding to respective positions of the material to be tested, the corresponding pixel to the detected candidate flaw position having a gray level capable of being identified from the other pixels, in correspondence to a phase of the candidate flaw signal at the candidate flaw position;

evaluating a continuity of the candidate flaw position with regard to a direction corresponding to the phase of the candidate flaw signal at the candidate flaw position existing in each of the testing images, by individually applying an image processing to each of the testing images; and detecting the flaw based on the continuity of the candidate flaw position.

3. The magnetic testing method according to claim 1, wherein frequencies of the first current and the second current satisfy the following equation (1), frequency of first current/frequency of second current$\geq 8$ (1).

4. A magnetic testing apparatus comprising:
a magnetizing device applying a rotating magnetic field to a material to be tested;
a detecting device detecting a testing signal generated by the rotating magnetic field; and
a signal processing device applying a signal processing to the testing signal,
wherein the magnetizing device is provided with an exciting coil applying an alternating current obtained by superimposing a first current and a second current having a lower frequency than the first current as an exciting current, and
wherein the signal processing device includes:
a first synchronous detecting device synchronously detecting the testing signal detected by the detecting device by using the first current as a reference signal;
a second synchronous detecting device synchronously detecting an output signal of the first synchronous detecting device by using the second current as a reference signal so as to extract a candidate flaw signal; and
a testing image display device displaying a testing image constructed by a plurality of pixels corresponding to respective positions of the material to be tested, each of the pixels having a gray level corresponding to an intensity of the candidate flaw signal at each of the positions, and a phase of the candidate flaw signal at each of the positions in the testing image being capable of being identified.

5. A magnetic testing apparatus comprising:
a magnetizing device applying a rotating magnetic field to a material to be tested;
a detecting device detecting a testing signal generated by the rotating magnetic field; and
a signal processing device applying a signal processing to the testing signal,
wherein the magnetizing device is provided with an exciting coil applying an alternating current obtained by superimposing a first current and a second current having a lower frequency than the first current as an exciting current, and
wherein the signal processing device includes:
a first synchronous detecting device synchronously detecting the testing signal detected by the detecting device by using the first current as a reference signal;
a second synchronous detecting device synchronously detecting an output signal of the first synchronous detecting device by using the second current as a reference signal so as to extract a candidate flaw signal;
a candidate flaw position detecting device detecting a candidate flaw position in the material to be tested by binarizing the candidate flaw signal by a predetermined threshold value;
a testing image forming device forming a plurality of testing images which are constructed by a plurality of pixels corresponding to respective positions of the material to be tested, the pixel corresponding to the detected candidate flaw position having a gray level capable of being identified from the other pixels, in correspondence to a phase of the candidate flaw signal in the candidate flaw position;
a continuity evaluating device evaluating a continuity of the candidate flaw position with regard to a direction corresponding to a phase of the candidate flaw signal at the candidate flaw position existing in each of the testing images, by individually applying an image processing to each of the testing images; and
a flaw detecting device detecting the flaw based on the continuity of the candidate flaw position.

6. The magnetic testing apparatus according to claim 4, wherein frequencies of the first current and the second current satisfy the following equation (1), frequency of first current/frequency of second current$\geq 8$ (1).

7. The magnetic testing method according to claim 2, wherein frequencies of the first current and the second current satisfy the following equation (1), frequency of first current/frequency of second current$\geq 8$ (1).

8. The magnetic testing apparatus according to claim 5, wherein frequencies of the first current and the second current satisfy the following equation (1), frequency of first current/frequency of second current$\geq 8$ (1).

* * * * *